United States Patent [19]

Petta et al.

[11] Patent Number: 5,693,311
[45] Date of Patent: Dec. 2, 1997

[54] POLYIODINATED COMPOUNDS, PROCESS FOR PREPARING THEM AND DIAGNOSTIC COMPOSITIONS

[75] Inventors: Myriam Petta, Aulnay-sous-Bois; Dominique Meyer, Saint-Maur, both of France

[73] Assignee: Guerbet S.A., Villepinte, France

[21] Appl. No.: 406,304

[22] Filed: Mar. 17, 1995

[30] Foreign Application Priority Data

Mar. 22, 1994 [FR] France ................... 94 03356

[51] Int. Cl.$^6$ ................... A61K 49/04; C07C 233/67
[52] U.S. Cl. ................... 424/9.455; 514/616; 514/617; 564/153; 564/155; 564/156
[58] Field of Search ................... 564/156, 153, 564/155; 424/9.455; 514/616, 617

[56] References Cited

U.S. PATENT DOCUMENTS 4,364,921  12/1982  Speck et al. ................... 424/5

FOREIGN PATENT DOCUMENTS 881510    11/1961  United Kingdom.
WO9208691  5/1992  WIPO.

OTHER PUBLICATIONS

Suter et al., Helv. Chim. Acta, vol. 54, Fasc 7, pp. 2097–2107, 1971.

*Primary Examiner*—Shailendra Kumar
*Attorney, Agent, or Firm*—Jacobson, Price, Holman & Stern, PLLC

[57] ABSTRACT

A compound of the following formula II

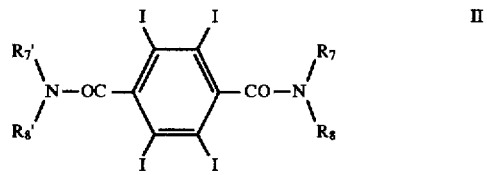

in which $R_7$, $R_8$, $R'_7$, $R'_8$, collectively, contain 10–24 hydroxyl groups and are selected, independently, from H, $(C_1-C_{10})$alkyl, $(C_1-C_{10})$alkyl substituted with one or more radicals selected from hydroxyl groups, $(C_1-C_3)$alkoxy groups and hydroxylated $(C_1-C_3)$alkoxy groups, is useful as a contrast agent in diagnostic X-Ray radiography.

10 Claims, No Drawings

POLYIODINATED COMPOUNDS, PROCESS FOR PREPARING THEM AND DIAGNOSTIC COMPOSITIONS

The present invention relates to polyiodinated compounds, to the process for preparing them and to their use as contrast agent during X-ray radiographies in man.

These compounds are benzene derivatives, substituted by 4 or 5 iodine atoms.

Tetraiodinated or pentaiodinated benzene derivatives have already been mentioned among other contrast agents, especially in Patents FR 828 486, U.S. Pat. No. 3,042,715, CH 615 344 and GB 881 510. All these derivatives contained at least one carboxylic or amino group, such that some of their salts exhibited the aqueous solubility required for their administration by injection. However, it is known that the osmolality of a solution of contrast agent, which increases with the ion concentration of the medium, may be responsible for side effects during the injection when it is considerably greater than that of the biological medium.

It was therefore desirable to find compounds with a high percentage by weight of iodine, so as to be able to reduce the dose of contrast agent injected into the human subject, which are soluble in water so that the total volume injected remains between the usual limits, from 10 to 300 ml according to the organ to be visualized, and the solutions of which have an osmolality less than that of the compounds previously mentioned, as well as a moderate viscosity.

The compounds according to the invention are of formula:

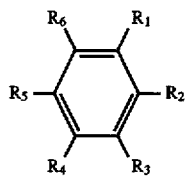
(I)

in which $R_1$, $R_2$, $R_3$, $R_4$, $R_5$, $R_6$ are selected independently from the iodine atom and the groups:

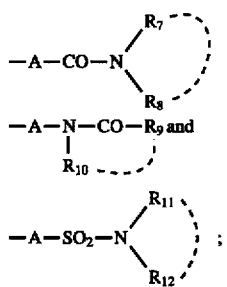

in which A represents nothing or ($C_1$–$C_4$)alkylene, which is optionally hydroxylated;

$R_7$, $R_8$, $R_9$, $R_{10}$, $R_{11}$ and $R_{12}$, which are identical or different, represent H, ($C_1$–$C_{10}$)alkyl, which is optionally hydroxylated or carrying one or more ($C_1$–$C_3$)alkoxy groups, which are optionally hydroxylated or, with the nitrogen atom to which they are attached, $R_7$ and $R_8$, $R_9$ and $R_{10}$ or $R_{11}$ and $R_{12}$ can form independently a 5- to 8-membered saturated heterocycle, which is optionally hydroxylated, with the proviso that at least 4 groups among $R_1$, $R_2$, $R_3$, $R_4$, $R_5$ and $R_6$ represent the iodine atom and that the compounds of formula I contain 10 to 24 hydroxyl groups.

The alkyl, alkoxy, alkylene groups are linear or branched.

The tetraiodinated compounds of formula I in which the other two substituents represent:

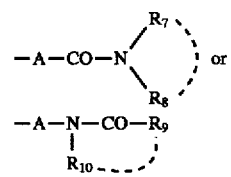

A being $CH_2$ or nothing, and particularly those for which A is nothing, $R_2$=$R_3$=$R_5$=$R_6$=I and $R_1$ and $R_4$ represent independently a hydroxylated —CO—NR$_7$R$_8$ group or a hydroxylated —N(R$_{10}$)—CO—R$_9$ group, are preferred.

Advantageously, the compounds of formula I carry 12 to 20 hydroxyl groups, preferably 12 to 16 hydroxyl groups and at least 2 groups among $R_7$, $R_8$, $R_9$ and $R_{10}$ represent —(CH$_2$)$_m$—(CHOH)$_n$—CH$_2$OH and m=1 or 2, n=0 to 4;

and p=0 to 3; or —C(CH$_2$OH)$_3$.

The tetraiodinated compounds which contain two amido, groups at the para position, identical or different, of formula:

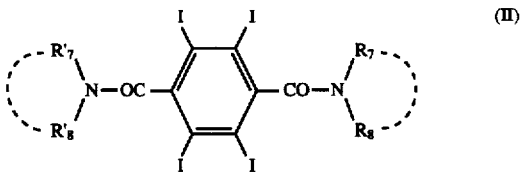
(II)

in which $R_7$, $R_8$, $R'_7$ and $R'_8$, which are identical or different, have the same meaning as $R_7$ and $R_8$ in formula I, are particularly preferred, especially for their tolerance and their ease of synthesis.

When the two amido groups are different, it is preferable that each contains at least two hydroxyl groups, especially for a more balanced distribution of the hydrophilicity.

When the two amido groups are identical, it is preferable that the compound of formula II contains 12 to 20 hydroxyl groups and that $R_7$ and $R_8$ are selected from the groups —CH$_2$—(CHOH)$_n$—CH$_2$OH with n=0 to 4, and

with p=1 or 3 and better still, that they are selected from the —CH$_2$—(CHOH)$_n$—CH$_2$OH groups with n=0 to 3, the said compound of formula II containing, in this case, from 12 to 16 hydroxyl groups, especially so as to have soluble products which are not very viscous.

The preparation of certain compounds of formula I or II of the invention uses the amino alcohols of formula HNR$_7$R$_8$, HNR'$_7$.R'$_8$ or HNR$_{11}$R$_{12}$.

Numerous hydroxylated amino alcohols are known and even marketed.

Among the latter, there may be mentioned:

(i) 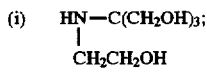

(ii) 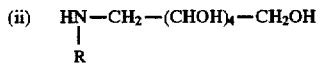

-continued with R = CH$_3$, CH$_2$CH$_2$OH; or

CH$_2$(CHOH)$_4$CH$_2$OH (iii) HN–[cyclohexane ring with two OH groups]

and (iv) glucosamine.

Other amino alcohols are described in the literature; they are prepared for instance by monosubstitution of primary amino alcohols or by disubstitution of benzylamine followed by debenzylation, under conventional conditions, especially by the action of H$_2$.

Among the commercially available primary amino alcohols, there may be mentioned: H$_2$N—CH$_2$—CHOH—CH$_3$, H$_2$N—CH$_2$—CHOH—CH$_2$OH, H$_2$N—(CH$_2$)$_3$—CH$_2$OH, H$_2$N—CH(CH$_2$OH)$_2$, H$_2$N—C(CH$_2$OH)$_3$ and $$H_2N-\underset{\underset{R_b}{|}}{\overset{\overset{R_a}{|}}{C}}-CH_2OH$$

with R$_1$=H, R$_b$=CH$_3$ or C$_2$H$_5$; alternatively R$_a$=CH$_3$, R$_b$=CH$_2$OH.

Among the preferred known amino alcohols, there may be mentioned:

$$HN-CH_2-CHOH-CH_2OH$$
$$|$$
$$R$$

with R=CH$_3$, which is described in WO 89/10752
with R=CH$_2$CH$_2$OH, which is described in U.S. Pat. No. 5,075,502
with R=C(CH$_2$OH)$_3$ which is described in J. Amer. Chem. Soc., 66, 881 (1944);

and those described in EP-A-558 395, which are:

$$H-N-CH_2-(CHOH)_2-CH_2OH$$
$$|$$
$$R$$

with R=CH$_3$, CH$_2$—CH$_2$—OH, CH$_2$—CHOH—CH$_2$OH, CH$_2$—(CHOH)$_2$—CH$_2$OH and CH(CH$_2$OH)$_2$;

$$H-N-CH-CHOH-CH_2OH$$
$$|\quad|$$
$$R\quad CH_2OH$$

with R=H, CH$_3$, CH$_2$CH$_2$OH, CH$_2$—CHOH—CH$_2$OH or CH(CH$_2$OH)$_2$ and $HN-CH_2-C(CH_2OH)_3$
$|$
$R$ with R=CH$_3$, CH$_2$CH$_2$OH and CH$_2$—CHOH—CH$_2$OH or alternatively those described in EP-A-25083 which are:

$$HN-CH(CH_2OH)_2$$
$$|$$
$$R$$

with R=CH$_3$, C$_2$H$_5$, CH$_2$CH$_2$OH, CH$_2$—CHOH—CH$_2$OH and CH(CH$_2$OH)$_2$.

Among the heterocyclic amino alcohols, there may be mentioned:

[cyclohexane ring with HN, R, and three OH groups]

R=H, OH which is described in Chem. Bar., 692, p. 200–214.

It is understood that the amides according to the invention are by no means limited to those prepared from the amino alcohols previously mentioned or already known.

The pentaiodinated compounds of formula I in which the last substituent is $$-CO-N\underset{R_8}{\overset{R_7}{\diagup}}$$

may be prepared by the action of an amino alcohol on pentaiodobenzoic acid chloride obtained by the action of thionyl chloride on pentaiodobenzoic acid which is described in J. Org. Chem. 49 (17) 3051–3053 (1984).

The tetraiodinated compounds of formula I containing two amido groups $$-CON\underset{R_8}{\overset{R_7}{\diagup}}$$

may be prepared from tetraiodoisophthalic and tetraiodoterephthalic acids, which are obtained by iodination of the corresponding diacids as described in FR-A-828 486.

In addition, the isophthalic derivatives can be obtained by a Sandmeyer reaction with KI on the diazo derivative of triiodoaminoisophthalic acid, which is known.

Conditions for amidation of benzoic acids containing, at the ortho position, two iodine atoms are known to persons skilled in the art and are described in numerous publications and patents.

There may be mentioned for example FR-A-2 354 316, FR-A-2 293 919, EP-A-15867, EP-A-32388 or EP-A-233249.

When the two amido groups are different, the amidation may be carried out as described in FR-A-2 023 741 by the action of a first amino alcohol, introduced in small portions, on an activated derivative, in the form of an acid halide, an ester or an anhydride, of the diacid, followed by the action of a second amino alcohol on the activated monoacid monoamide.

The amidation of the —A—COOH groups in which A is different from nothing may be carried out in a conventional manner.

The tetraiodinated compounds of formula I in which $R_2=R_3=R_5=R_6=I$;

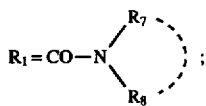

and

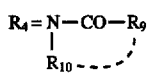

may be prepared from p-nitrotoluene by the following method:

1/ iodination of p-nitrotoluene to give 2,6-diiodo-4-nitrotoluene;

2/ action of N-bromosuccinimide to give the compound of formula:

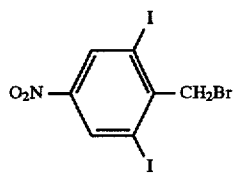

3/ oxidations to give 2,6-diiodo-4-nitrobenzaldehyde, then 2,6-diiodo-4-nitrobenzoic acid;

4/ reaction of an activated derivative of this acid with an amino alcohol to give

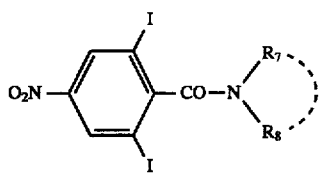

5/ catalytic reduction of the nitro group to an amino group;

6/ iodination of the compound obtained to give a tetraiodinated derivative;

7/ acylation of the amino group with an activated derivative of the acid $R_9$-COOH, the hydroxyl groups present having optionally been protected;

8/ substitution of the secondary amido group formed by the action of a compound of formula $R_{10}$-X" in which X" represents a halogen, and particularly Cl or Br or a $(C_1-C_4)$ alkylsulphonyl group such as the methylsulphonyl or $(C_6-C_{10})$arylsulphonyl group which is optionally substituted by a $(C_1-C_4)$alkyl such as the p-toluenesulphonyl group;

9/ where appropriate, deprotection of the hydroxyl groups.

The deprotection of the hydroxyl groups may be carried out before the substitution stage. Likewise, stages 7 and 8 can be interchanged, and the secondary aniline can be prepared by the action of $R_{10}$-X" before reacting an activated derivative of $R_9$-COOH.

The iodination reactions may be carried out, as is well known, with aqueous ICl, with $I_2$ in the presence of KI and $C_2H_5NH_2$ or $KICl_2$, with $I_2$ dissolved in oleum, or with an $I_2/H_5IO_6$ mixture.

The oxidation of the brominated derivative to an aldehyde may be carried out by the action of triethylamine N-oxide in a solvent, such as 1,2-dichloroethane; the oxidation of the aldehyde may be carried out with $KMnO_4$.

The amido groups may be obtained in a conventional manner, by reacting the corresponding acid chlorides with the appropriate amino alcohols, it being possible for the acid chlorides to be obtained by the action of $SOCl_2$ on the acid. If necessary, the free hydroxyl groups may be protected in the form of esters, especially acetic esters.

Some of the intermediate amino alcohols are new compounds and they are also a subject matter of the invention. These compounds correspond to the formula:

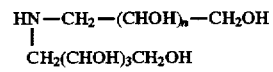

in which
n=1 to 3, to the formula:

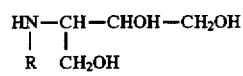

with $R=CH_2(CHOH)_pCH_2OH$ with p=2, 3, and to the formula:

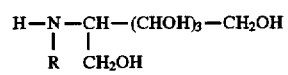

in which $R=CH_2(CHOH)_p-CH_2OH$ with p=1 to 3.

These compounds may be prepared by reductive amination of xylose, erythrose or fructose, with an amino alcohol or ammonia, and especially with hydrogen in the presence of a hydrogenation catalyst such as palladized charcoal.

The invention also relates to the diagnostic compositions which are useful as contrast agents during X-ray radiographies in man, for example, to carry out angiographies or urographies or to opacify various body regions.

These compositions, in the form of solutions or optionally of suspensions or emulsions, containing between 10 and 40 g of iodine groups per 100 ml, can be administered enterally or parenterally. The solutions are in general aqueous solutions, preferably buffered; they my comprise various additives, such as $Na^+$, $Ca^{2+}$, $Mg^{2+}$ cations, stabilizers such as calcium edetate, osmolar agents.

These compositions can also be administered orally or rectally, especially for visualizing the gastrointestinal system.

The unit doses will be a function of the region to be observed and the human subject treated; for injectable solutions, they will be in general from 10 to 300 ml.

In the text which follows, examples of compounds of the invention are described.

The thin-layer chromatographies were carried out on silica gel plates marketed by MERCK under the reference F-254, using as eluent, unless otherwise stated, a mixture $S_1$ of $H-CO_2H/CH_3-CO-C_2H_5/C_6H_5-CH_3$ (25/25/60 -v/v/v), developing under ultraviolet radiation, or for the amino alcohols with ninhydrin, the eluent being the mixture $(C_2H_5OH/25\%$ aqueous $NH_4OH$: 7/3 - v/v).

The $^{13}C$ NMR spectra were, unless otherwise stated, carried out with an apparatus at 200 MHz in DMSO (dimethyl sulphoxide) as internal standard.

First, the preparation of various amino alcohols, used in the examples below, is indicated.

A) 5-(2,3-Dihydroxypropylamino)-1,2,3,4-pentanetetrol ($HNR_7R_8$: $R_7=CH_2-CHOH-CH_2OH$, $R_8=CH_2-(CHOH)_3-CH_2OH)$ A mixture of 529.5 g of commercially available D-xylose and 289 g of amino-2,3-propanediol in 12.5 l of ethanol, in the presence of 53 g of 10% palladized charcoal is hydrogenated at a pressure of $6\times10^5$ Pa, at 50° C. for 30 hours. The catalyst is then removed by filtration on Celite and the filtrate concentrated to dryness. The residual oil dissolved in 30 l of water is passed over 3 l of resin in the H$^+$ form, reference IRC 50, from Rohm and Haas. 616 g of the desired amino alcohol are thus isolated.

TLC: Rf=0.3

$^{13}$C NMR: δ (ppm):

72-70 (CHOH); 65-63 (CH$_2$OH); 53-52 (CH$_2$NH).

B) 5-((1-Hydroxymethyl-2,3-dihydroxy)propylamino)-1, 2,3,4-pentanetetrol (HNR$_7$R$_8$: R$_7$=CH—CHOH—CH$_2$OH
             |
             CH$_2$OH 6 g of 2-amino-1,3,4-butanetriol, prepared by the method described in U.S. Pat. No. 4,439,613 and 8.2 g of commercially available D-xylose dissolved in 250 ml of ethanol, with 1 g of 10% palladized charcoal, are hydrogenated for 48 hours at 50° C. at a pressure of $8\times10^5$ Pa.

The catalyst is then removed by filtration on Celite and the filtrate concentrated under reduced pressure.

After passing over 80 ml of IRC 50 resin, 4.5 g of the expected amino alcohol are obtained.

TLC: Rf=0.28

$^{13}$C NMR: δ (ppm):

70–71 (CHOH); 64,63,60 (CH$_2$OH); 61 (CHNH); 50 (CH$_2$NH).

C) 5-(2,3,4,5-Tetrahydroxypentylamino)-1,2,3,4-pentanetetrol (HNR$_7$R$_8$: R$_7$=R$_8$=CH$_2$(CHOH)$_3$—CH$_2$OH)

A mixture of 26 g of D-xylose, 5.5 ml of a 25% (w/v) aqueous solution of NH$_4$OH in 345 ml of methanol is hydrogenated in the presence of 2.5 g of 10% palladized charcoal at a pressure of $8\times10^5$ Pa at 50° C. for 48 hours.

After removing the catalyst, the solution is concentrated under reduced pressure and the residual oil passed over IRC 50 resin to give 2 g of the expected amino alcohol.

TLC: Rf=0.17

$^{13}$C NMR: δ (ppm):

72-71.5-70.5 (CHOH); 63 (CH$_2$OH); 51.4 (CH$_2$NH).

D) 5 -(2,3-Dihydroxypropylamino)-1,2,3,4,6-hexanepentol (HNR$_7$R$_8$: R$_7$=CH$_2$—CHOH—CH$_2$OH

R$_8$=CH—(CHOH)$_3$—CH$_2$OH)
     |
     CH$_2$OH

A mixture of 1.9 g of amino-2,3-propanediol, 4.5 g of commercially available fructose in 150 ml of methanol is hydrogenated for 6 hours at a pressure of $14\times10^5$ Pa at 80° C. in the presence of 2 g of palladized charcoal.

After filtration on Celite to remove the catalyst, the solution is concentrated; the residual oil dissolved in 10 ml of water is chromatographed on a resin in the H$^+$ form (IRN 77), eluting with an aqueous solution of NH$_4$OH of increasing concentration.

2.1 g of the expected product are finally isolated in the form of an oil.

TLC: Rf=0.25

$^{13}$C NMR: 67-74 (CHOH); 64 (CH$_2$OH); 62 (CH—CH$_2$OH); 50 (CH$_2$CH).

By applying the preceding procedure, 4-((1-hydroxymethyl)-2,3-dihydroxy)propylamino)-1,2,3-butanetriol is prepared from erythrulose and H$_2$N—CH$_2$(CHOH)$_2$—CH$_2$OH.

(HNR$_7$R$_8$: R$_7$=CH—CHOH—CH$_2$OH
             |
             CH$_2$OH

TLC: Rf=0.55

E) 5-(2,3,4-Trihydroxybutylamino)-1,2,3,4-pentanetetrol (HNR$_7$R$_8$: R$_7$=CH$_2$—(CHOH)$_2$—CH$_2$OH

R$_8$=CH$_2$—(CHOH)$_3$—CH$_2$OH)

i) butene-3,4-diol: H$_2$C=CH—CHOH—CH$_2$OH 250 g of commercially available cis-2-butene-1,4-diol are dissolved in 1 500 ml of water containing 15 ml of a 10N aqueous solution of HCl and 3 g of CuCl. After 16 hours at the reflux temperature, the pH of the mixture, readjusted about room temperature is brought to 7 by addition of a 2N aqueous solution of NaOH, then the reaction medium is filtered on 500 g of Celite (diatomaceous silica).

The water is then removed under reduced pressure and the oily residue distilled to give 86 g of the expected product.

b.p.=70° C. at 200 Pa

TLC (CH$_2$Cl$_2$/CH$_3$OH: 90/10: v/v)

Rf=0.7 ii) N,N-Dibenzylamino-2,3,4 -butanetriol ((C$_6$H$_5$—CH$_2$)$_2$N—CH$_2$—(CHOH)$_2$—CH$_2$OH)

31.4 g of the oil obtained, 1 g of H$_2$WO$_4$ and 1.4 g of CH$_3$COONa are introduced into 120 ml of water, and then 20.5 ml of 50% H$_2$O$_2$ are added dropwise.

After stirring for 6 hours, 23.4 g of dibenzylamine dissolved in 300 ml of ethanol are slowly introduced. The mixture is kept stirring for 18 hours at 40° C. before being concentrated under reduced pressure. The residue crystallizes from ethyl ether. 30 g of the expected product are isolated.

m.p.=95° C.

iii) 1-Amino-2,3,4-butanetriol (H$_2$—CH$_2$—(CHOH)$_2$—CH$_2$OH)

17 g of the preceding product dissolved in 400 ml of ethanol are hydrogenated at 50° C. at a pressure of $7\times10^5$ Pa in the presence of 3.5 g of palladized charcoal (10%) for 7 hours. After removing the catalyst and concentrating under reduced pressure, the residual oil is chromatographed, eluting with a CH$_3$OH/25% aqueous NH$_4$OH mixture (8/2, v/v) on silica to give 4.5 g of the pure amino alcohol.

$^{13}$C NMR: δ (ppm): 72 (CHOH); 62 (CH$_2$OH); 45 (CH$_2$N)

iv) 1.4 g of the primary amino alcohol previously isolated and 1.93 g of xylose dissolved in 70 ml of methanol are hydrogenated at a pressure of $12\times10^5$ Pa, at 50° C. for 6 hours in the presence of 0.7 g of palladium on charcoal (10%). After removing the catalyst by filtration, the mixture is concentrated to dryness. The residue dissolved in the minimum of water is chromatographed on an IRN 77 resin (H$^+$), eluting with an aqueous solution of NH$_4$OH of increasing concentration.

After removing the solvent, 1.5 g of the expected oily product are isolated.

TLC: Rf=0.3

$^{13}$C NMR: δ (ppm): 70–75 (CHOH); 63 (CH$_2$OH); 52 (N(CH$_2$)$_2$).

EXAMPLE 1

N,N'-bis[(2-Hydroxyethyl) (2,3,4,5,6-pentahydroxyhexyl]-2,4,5,6- tetraiodo-1,3-isophthalamide (Formula I:
R$_2$=R$_4$=R$_5$=R$_6$=I;
R$_1$=—CO—NR$_7$R$_8$;
R$_3$=—CO—NR'$_7$R'$_8$;
R$_7$=R'$_7$=CH$_2$—CH$_2$OH; and
R$_8$=R'$_8$=CH$_2$—(CHOH)$_4$—CH$_2$OH).

1/ Tetraiodoisophthalic acid 2.07 g (0.03 mol) of NaNO$_2$ dissolved in 30 ml of water are introduced dropwise at 5° C. over 11.2 g (0.02 mol) of 5-amino-2,4,6-triiodophenyl-1,3-dicarboxylic acid dissolved in 60 ml of a 1N aqueous solution of NaOH. The pH of the solution is brought to 2 by addition of concentrated sulphuric acid and the stirring is continued for 3 hours at 5° C. 9.6 g (0.06 mol) of KI dissolved in 20 ml of water are then introduced dropwise into the reaction medium, previously brought to pH 5 by addition of an aqueous solution of sodium hydroxide. The mixture is then slowly heated to 45° C. at which temperature it is maintained for 2 hours before being cooled to room temperature. It is then poured into 500 ml of a mixture of ice and 1N aqueous solution of hydrochloric acid. The precipitate formed is washed with an aqueous solution of sodium bisulphite and then with 150 ml of CH$_2$Cl$_2$ to give 11 g of substantially pure beige crystals of the expected product (97.5% of the theory as I) , 82% yield.

TLC (eluent S$_1$)–Rf=0.7

$^{13}$C NMR: δ (ppm): 168 (CO$_2$H); 148 (C-CO); 127, 105, 89 (C-I).

2/ Tetraiodoisophthalic acid dichloride 10.4 g (0.015 mol) of the diacid, 150 ml of SOCl$_2$ and 0.2 ml of dimethylformamide (DMF) are maintained for 8 hours at the reflux temperature. SOCl$_2$ is then removed under reduced pressure and the residue is solidified by scraping in 100 ml of petroleum ether to give 11 g of beige crystals containing 98% of the calculated quantity of iodine and 101% chlorine.

TLC (eluent S$_1$)–Rf=0.1

3/ N,N'-bis[(2-Hydroxyethyl) (2,3,4,5,6-pentahydroxyhexyl )]-2,4,5,6-tetraiodo-1,3-isophthalamide 11 g (0.015 mol) of the acid dichloride are added, in portions, to a solution of 10.5 g (0.0465 mol) of commercially available 1-deoxy-1-(2-hydroxyethylamino)-D-glucitol dissolved in 120 ml of dimethylacetamide (DMAC) containing 6.4 ml of triethylamine. The mixture is kept stirring for 24 hours at 60° C., the triethylamine salt is removed by filtration and the filtrate is concentrated under vacuum. The oil obtained is treated with resin in the H$^+$ form marketed by Rohm and Haas under the reference IRN 77 and the resin under the form OH$^-$ marketed under the reference IRA 67, and then chromatographed on silica, eluting with a CH$_2$Cl$_2$/CH$_3$OH mixture (35/65: v/v) .

4.2 g of crystals of the expected product are isolated whose iodine content is 98% of that expected.

TLC (CH$_2$Cl$_2$/CH$_3$OH: 40/60: v/v)–Rf=0.2

$^{13}$C NMR: δ (ppm): 120 (C=O); 148 (C-CO); 128, 108, 92 (C-I); 69 to 73 (CH$_2$CHOH); 57 to 62 (CH$_2$OH); 48 and 52 N(CH$_2$)$_2$.

EXAMPLE 2

N,N'-bis[(2-Hydroxyethyl) (2,3,4,5,6-pentahydroxyhexyl]-2,3,5,6-tetraiodo-1,4-phenylenediacetamide (Formula I: R$_2$=R$_3$=R$_5$=R$_6$=I; R$_1$=R$_4$=CH$_2$—CONR$_7$R$_8$ and R$_7$=CH$_2$—CH$_2$OH; R$_8$=CH$_2$—(CHOH)$_4$—CH$_2$OH).

1/ 2,3,5,6-Tetraiodo-1,4-phenylenediacetic acid 10 g (51.5 mmol) of commercially available 1,4-phenylenediacetic acid are slowly introduced into a mixture of 9.2 g (40.5 mmol) of periodic acid, 200 ml of concentrated sulphuric acid and 30.9 g (121.5 mmol) of iodine, at 0° C. After stirring for 1 hour at this temperature, the mixture is maintained at 35° C. for 48 hours and then poured over an ethyl acetate/ice mixture (2½00 ml). The precipitate formed is washed with 250 ml of CH$_2$Cl$_2$ and of CH$_3$COOC$_2$H$_5$ to give a beige powder (96% of theory as iodine).

TLC (eluent S$_1$): Rf=0.63

$^{13}$C NMR: δ (ppm): 169 (CO$_2$H); 143 (C—CH$_2$); 116 (C-I); 62 (CH$_2$)

2/ 2,3,5,6 -Tetraiodophenylenediacetic acid dichloride 24.5 g (0.035 mol) of 2,3,5,6-tetraiodophenylene-1,4-diacetic acid, 1.5 ml of DMF and 590 ml of SOCl$_2$ are maintained for 8 hours at reflux. After concentration under reduced pressure, the solid residue is washed with 100 ml of CH$_2$Cl$_2$. After washing with 250 ml of petroleum ether, 10.7 g of the expected product are obtained (percentage as I: 98.5% of theory, as Cl: 101.4%).

TLC (eluent S$_1$): Rf=0.67.

3/ N,N'-bis[(2-Hydroxyethyl) (2,3,4,5,6-pentahydroxyhexyl)]-2,3,5,6 - tetraiodo -1,4-phenylenediacetamide 10.5 g (14 mmol) of the acid dichloride dissolved in 90 ml of DMAC are added dropwise to a solution of 11 g (49 mmol) of 1-deoxy-1-(2-hydroxyethylamino)-D-glucitol, 4.9 g (49 mmol) of triethylamine in 90 ml of DMAC.

The mixture is kept stirring for 2 days at 50° C. before concentrating under reduced pressure. 250 ml of water are introduced and the precipitate which appears is isolated by filtration and washed thoroughly with water. 14.8 g of the expected product are thus obtained in the form of a white powder which contains 93.6% of the theoretical quantity of iodine.

TLC (CH$_2$Cl$_2$/CH$_3$OH: 40/60: v/v): Rf=0.2

$^{13}$C NMR: δ (ppm): 168 (C=O); 145 (C—CH$_2$); 118 (C-I); 69 to 74 (CHOH); 63 (CH$_2$OH); 62 (CH$_2$CO); 59 (CH$_2$OH); 51 (NCH$_2$); 49 (NCH$_2$).

EXAMPLE 3

N,N'-bis[(2-Hydroxyethyl) (2,3,4,5,6-pentahydroxyhexyl]-2,3,5,6-tetraiodoterephthalamide (Formula II:
R$_7$=R'$_7$=CH$_2$—CH$_2$OH; R$_8$=R'$_8$=CH$_2$—(CHOH)$_4$—CH$_2$OH)

b 94.2g (0.42 mol) of commercially available 1-deoxy-1-(2-hydroxyethylamino)-D-glucitol dissolved in 850 ml of DMAC are introduced dropwise, at 50° C., into a solution of 98.5 g (0.14 mol) of the acid dichloride in 850 ml of DMAC and 42.3 g (0.42 mol) of triethylamine. After stirring for 2 days at 60° C., the medium is concentrated under reduced pressure and the oil obtained purified by passing over the IRN 77 and IRA 67 resins, and then by chromatography at a pressure of 52×10$^5$ Pa on a graft silica column (Kromasil 100 C18 -10 µm of EKA NOBEL), with an $H_2O/CH_3OH$ gradient and a flow rate of 120 ml/minute.

TLC ($CH_2Cl_2/CH_3OH$: 40/60: v/v): Rf=0.2

$^{13}C$ NMR: δ (ppm): 171 (C=O); 148 (C-CO); 110 (C-I); 69 to 72 (CHOH); 63 and 58 ($CH_2OH$).

EXAMPLE 4

N,N'- tetrakis (2,3,4-Trihydroxybutyl)-2,3,5,6-tetraiodoterephthalamide (Formula II: $R_7=R'_7=R_8=R'_8=CH_2—(CHOH)_2—CH_2OH$ Using the procedure of Example 3, starting with the same diacid and 2,3,4-trihydroxybutylamino-1,2,3-butanetriol, the expected product is obtained.

TLC ($CH_2Cl_2/CH_3OH$: 60/40: v/v): Rf=0.2

$^{13}C$ NMR: δ (ppm): 171 (C=O); 148 (C-CO); 110 (C-I); 66 to 73 (CHOH); 62 ($CH_2OH$); 49 to 54 ($NCH_2$).

EXAMPLE 5

N,N'-bis[(2,3-Dihydroxypropyl) (2,3,4-trihydroxybutyl)]-2,3,5,6- tetraiodoterephthalamide (Formula II:

$R_7=R'_7=CH_2—CHOH—CH_2OH$;

$R_8=R'_8=CH_2—(CHOH)_2—CH_2OH$)

5.85 g (0.03 mol) of 5-(2,3-dihydroxypropylamino)-2,3,4-butanetriol dissolved in 75 ml of DMAC are introduced dropwise into a solution of 7.07 g (0.01 mol) of the acid dichloride, of 4.17 ml (0.03 mol) of triethylamine and of 75 ml of DMAC. The mixture is kept stirring overnight at 60° C. and then concentrated under reduced pressure. The oily residue is dissolved in 20 ml of a 1/1 $CH_2Cl_2/C_2H_5OC_2H_5$ mixture (v/v) and purified by passing over an IRN 77 and then IRA 67 resin and chromatographed on 40 g of silica, eluting with a 1/1 $CH_2Cl_2/CH_3OH$ mixture (v/v).

2.5 g of the expected product are thus obtained in the form of a white .powder whose iodine titre is 97.2% of theory.

TLC ($CH_2Cl_2/CH_3OH$: 60/40: v/v): Rf=0.2

$^{13}C$ NMR: δ (ppm): 174 (C=O); 150 (C-C=O); 112 (C-I); 70 to 76 (CHOH); 63 to 65 ($CH_2OH$); 51 to 55 ($CH_2N$).

EXAMPLE 6

N,N'-bis[(2,3-Dihydroxypropyl ) (2,3,4,5-tetrahydroxypentyl)]-2,3,5,6-tetraiodoterephthalamide (Formula II:

$R_7=R'_7=CH_2—CHOH—CH_2OH$;

$R_8=R'_8=CH_2—(CHOH)_3—CH_2OH$)

100 g (0.44 mol) of 5-(2,3-dihydroxypropylamino)-1,2,3,4-pentanetetrol dissolved in i 130 ml of DMAC are introduced dropwise, at 55° C., into a solution of 103.5 g (0.15 mol ) of the 2,3,5,6- tetraiodoterephthalic acid dichloride in 1 130 ml of DMAC containing 57 g (0.56 mol) of triethylamine. After stirring for 3 days at this temperature, the reaction medium is concentrated and the oil obtained is chromatographed on 1 l of IRM 77 and then IRA 67 resin before being chromatographed at a pressure of $52 \times 10^5$ Pa on a graft silica column (Kromasil 100 C18 -10 µm of EKA NOBEL) with an $H_2O/CH_3OH$ gradient and a flow rate of 120 ml/minute to give 43 g (0.04 mol) of the expected product, substantially pure.

TLC ($CH_3OH$): Rf=0.2

$^{13}C$ NMR: δ (ppm): 171.6 (C=O); 149.2 (C-CO); 110.8 (C-I); 73-69 (CHOH); 65-62 ($CH_2OH$); 54-50 ($CH_2N$).

EXAMPLE 7

N,N'-bis[(2,3 -Dihydroxypropyl) (2,3,4,5,6-pentahydroxyhexyl)]-2,3,5,6-tetraiodoterephthalamide (Formula II:

$R_7=R'_7=CH_2—CHOH—CH_2OH$;

$R_8=R'_8=CH_2—(CHOH)_4—CH_2OH$)

66.4 g (0.26 mol) of 5-(2,3-dihydroxypropylamino)-1,3,4,5,6-hexanepentol, prepared as described in U.S. Pat. No. 2,258,834, dissolved in 560 ml of DMAC, are introduced dropwise, at 60° C., into a solution, in 560 ml of DMAC, of 61.3 g (0.087 mol) of 2,3,5,6-tetraiodoterephthalic acid dichloride and 26.3 g (0.26 mol) of triethylamine.

After stirring for 3 days at 60° C., the mixture is concentrated under reduced pressure. The residual oil is passed over the IRN 77 and IRA 67 resins and then purified by preparative chromatography as in the preceding example.

32.1 g (0.028 mol) of the expected compound are thus obtained substantially pure.

TLC ($CH_3OH/CH_2Cl_2$: 60/40: v/v): Rf=0.16

$^{13}C$ NMR: δ (ppm): 171.6 (C=O); 148.6 (C-CO); 111 (C-I); 73-69 (CHOH); 63 ($CH_2OH$); 54-51 ($CH_2—N$).

EXAMPLE 8

N,N'- tetrakis(2,3,4,5,6-Pentahydroxyhexyl)-2,3,5,6-tetraiodoterephthalamide (Formula II: $R_7=R'_7=R_8=R'_8=CH_2—(CHOH)_4—CH_2OH$)

58.7 g (0.17 mol) of commercially available disorbitylamine dissolved in 750 ml of DMAC are introduced dropwise, at 65° C., into a solution of 31.2 g (0.04 mol) of the acid dichloride, of 17.2 g (0.17 mol) of triethylamine and of 750 ml of DMAC. After stirring for 3 days at 70° C. and overnight at room temperature, the reaction medium is concentrated under reduced pressure and the residual oil passed over the IRN 77 and IRA 67 resins and then chromatographed in a preparative high-pressure chromatographic apparatus, under the same conditions as in Example 6.

11.6 g (8.8 mmol) of the expected product are thus obtained substantially pure.

TLC ($CH_3OH$): Rf=0.15

$^{13}C$ NMR: δ (ppm):172 (C=O );149 (C-C=O); 111.4 (C-I); 71.4 (CHOH); 63.3 ($CH_2OH$); 54-50 ($CH_2N$).

EXAMPLE 9

N,N'- tetrakis (2,3,4,5- Tetrahydroxypentyl )-2,3,5,6-tetraiodoterephthalamide (Formula II: $R_7=R'_7=R_8=R'_8=CH_2—(CHOH)_3—CH_2OH$)

Following the procedure of Example 10, starting with 1.3 g of acid dichloride and 1.7 g of the appropriate amino alcohol, but leaving the reaction medium for only 24 hours at 50° C. after the end of the addition, 800 mg of the expected product are obtained.

TLC ($CH_3OH/CH_2Cl_2$: 70/30: v/v): Rf=0.25

$^{13}C$ NMR: δ (ppm): 171 (C=O); 149 (C-C=O); 110 (C-I); 73-69 (CHOH); 62 ($CH_2OH$); 54-50 ($CH_2N$).

EXAMPLE 10

N,N'-bis[(2,3,4- Trihydroxybutyl) (2,3,4,5-tetrahydroxypentyl)]-2,3,5,6-tetraiodoterephthalamide (Formula II:
$R_7=R'_7=CH_2-(CHOH)_2-CH_2OH$
$R_8=R'_8=CH_2-(CHOH)_3-CH_2OH$)

By applying the method described in Example 9 to 1.4 g of acid chloride and 3.9 g of the appropriate amino alcohol, 700 mg of the expected product are obtained substantially pure.

TLC ($CH_3OH/CH_2Cl_2$: 60/40: v/v): Rf=0.15

$^{13}C$ NMR: δ (ppm): 171 (C=O); 148 (C-CO); 110 (C-I); 73-68 (CHOH); 62 ($CH_2OH$); 54-50 ($NCH_2$).

We claim:

1. A compound of the following formula II

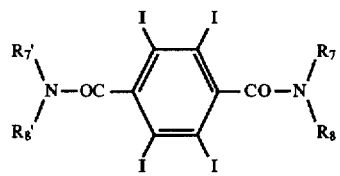

in which $R_7$, $R_8$, $R'_7$, $R'_8$, collectively, contain 10–24 hydroxyl groups and are selected, independently, from H, ($C_1-C_{10}$)alkyl, ($C_1-C_{10}$)alkyl substituted with one or more radicals selected from hydroxyl groups, ($C_1-C_3$)alkoxy groups and hydroxylated ($C_1-C_3$)alkoxy groups.

2. A compound according to claim 1 of formula II, in which $-NR_7R_8$ and $-NR'_7R'_8$ are different and each contains at least two hydroxyl groups.

3. A compound according to claim 1 of formula II, in which $-NR_7R_8$ and $-NR'_7R'_8$ are identical.

4. A compound according to claim 1, in which $-NR_7R_8$ and $-NR'_7R'_8$ are identical and $R_7$, $R_8$, $R'_7$, and $R'_8$, collectively, contain 12–20 hydroxyl groups and are selected, independently, from $-(CH_2)_m-(CHOH)_n-CH_2OH$ with m=1 or 2, n=0 to 4, $-CH-(CHOH)_p-CH_2OH$ with p = 0 to 3, and
 |
 $CH_2OH$ $-C(CH_2OH)_3$.

5. A compound according to claim 1, containing 12 to 20 hydroxyl groups, of formula II, in which $NR_7R_8$, and $NR'_7R'_8$ are identical and $R_7$, $R_8$, $R'_7$, $R'_8$, are selected from the groups $CH_2-(CHOH)_n-CH_2OH$ with n=0 to 4, and $-CH-(CHOH)_p-CH_2OH$ with p = 1 or 3.
 |
 $CH_2OH$ 6. A compound according to claim 1, of formula II in which $NR_7R_8$ and $NR'_7R'_8$ are identical and $R_7$, $R_8$, $R'_7$, $R'_8$, are selected from the $CH_2-(CHOH)_n-CH_2OH$ groups with n=0 to 3, said compound of formula II containing 12 to 16 hydroxyl groups.

7. A compound according to claim 1 of formula II, in which $NR_7R_8$ and $NR'_7R'_8$ represent:

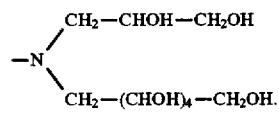

8. A compound according to claim 1 of formula II, in which $NR_7R_8$ and $NR'_7R'_8$ represent:

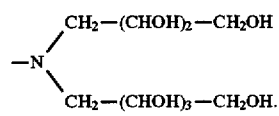

9. A diagnostic composition containing, as active ingredient, a compound of formula:

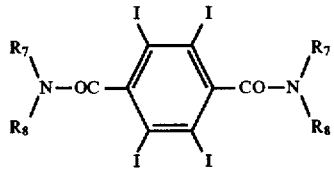

in which $R_7$ and $R_8$, collectively, contain 12–20 hydroxyl groups and are selected, independently, from the groups $-CH_2-(CHOH)_n-CH_2OH$ with n=0 to 4, and $-CH-(CHOH)_p-CH_2OH$ with p = 1 or 3.
 |
 $CH_2OH$ 10. A diagnostic composition, containing, as active ingredient, a compound of formula:

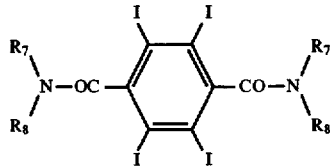

in which $R_7$ and $R_8$, collectively, contain 12–16 hydroxyl groups and are selected, independently, from the groups $-CH_2-(CHOH)_n-CH_2OH$ with n=0 to 3.

* * * * *